United States Patent [19]

Gerhard et al.

[11] Patent Number: 5,393,531

[45] Date of Patent: Feb. 28, 1995

[54] PROCESS FOR THE PREPARATION OF A PHARMACEUTICAL FORMULATION CONTAINING AT LEAST TWO DIFFERENT ACTIVE SUBSTANCES AND USE OF SUCH A FORMULATION

[76] Inventors: Gergely Gerhard, Gartengasse 8, A-1053 Vienna; Tritthart Wolfram, Allgäu 36, A-9400 Wolfsberg, both of Austria

[21] Appl. No.: 907,481

[22] Filed: Jul. 1, 1992

[30] Foreign Application Priority Data

Jul. 1, 1991 [CH] Switzerland ............ 1944/91

[51] Int. Cl.$^6$ .............................................. A61K 9/96
[52] U.S. Cl. ................................... 424/466; 424/480; 424/43
[58] Field of Search ............... 424/466, 482, 440, 43

[56] References Cited

U.S. PATENT DOCUMENTS

| | | | |
|---|---|---|---|
| 3,906,107 | 9/1975 | Somani et al. | 424/315 |
| 4,289,751 | 9/1981 | Windheuser | 424/466 |
| 4,684,516 | 8/1987 | Bhutani | 424/469 |
| 4,832,956 | 5/1989 | Gergely | 424/482 |
| 4,865,849 | 9/1989 | Conte et al. | 424/466 |
| 4,940,588 | 7/1990 | Sparks | 424/440 |
| 5,073,377 | 12/1991 | Alexander | 424/466 |
| 5,126,348 | 6/1992 | McMurray | 514/264 |

*Primary Examiner*—Thurman K. Page
*Assistant Examiner*—William E. Benston
*Attorney, Agent, or Firm*—Ostrolenk, Faber, Gerb & Soffen

[57] ABSTRACT

An aqueous solution or dispersion for oral intake of at least two different pharmaceutical active substances is prepared by dissolving or suspending at least two different effervescent, soluble and/or disintegrating mixtures in tablet or granule form, each of which contains a different active substance or a different active substance combination, in one and the same quantity of water. At least one of the tablets may be used only as a fragment, and at least one of the mixtures may weigh less than 2000 mg, preferably less than 1500 mg, in particular less than 1000 mg. In particular at least one of the mixtures contains diuretic, in particular hydrochlorothiazide and/or furosemide, and at least one of the further mixtures contains a beta-blocker and/or a vasodilator, in particular naftidrofuryl, calcium antagonist, ACE inhibitor or alpha-1-blocker. Such effervescent, soluble and/or disintegrating mixtures in tablet or granule form are preferably used for the treatment of hypertension. Other active substance combinations are suitable for the treatment of asthma or osteoporosis or for ulcer therapy.

8 Claims, No Drawings

PROCESS FOR THE PREPARATION OF A PHARMACEUTICAL FORMULATION CONTAINING AT LEAST TWO DIFFERENT ACTIVE SUBSTANCES AND USE OF SUCH A FORMULATION

The therapeutic treatment of various disease states very frequently necessitates—particularly in elderly people—the intake of various pharmaceutical substances, sometimes over weeks or months or even years, some of which have to be taken dally or even several times a day and others perhaps only every second day or even only once per week. Furthermore, the dose very often is to be individually set by the doctor for a certain patient and is to be varied with the passage of time. This is difficult to achieve with the conventional dosage forms of the tablets or sugar-coated tablets. On the one hand, the intake of tablets—again particularly in the case of elderly people who often have difficulties in swallowing—is found to be unpleasant, especially when a large number of such tablets have to be taken, sometimes at each mealtime; on the other hand, the variation of the dose is complicated: small sugar-coated tablets or tablets are difficult for the patient to divide up when it is intended, for example, to administer half or quarter tablets.

It is therefore the object of the invention to provide a dosage, form for two or more active substances which is easy to take even for elderly patients and/or those with swallowing difficulties, and which on the other hand allow the doctor very substantial freedom with regard to the individual dose and its variation over the duration of a treatment with medicaments. This object is surprisingly and satisfactorily achieved by the features of the invention. Further embodiments of the invention are also described.

In the past, always only one effervescent tablet has been dissolved in water. The reason for this was, on the one hand, that the effervescent tablet had a weight of 2 g of more, generally 3 to 4 g, and for complete dissolution therefore required at least 100 ml, preferably 200 to 250 ml of water for dissolution. However, many people—particularly elderly ones—do not readily consume such large quantities of liquid, a problem that would be further exacerbated if they had to take two or more such tablets.

On the other hand, an individual dose, in particular, for example, according to a stepwise plan, as is frequently used for the treatment of hypertension, would require a large number of such mixtures of different compositions, which would constitute an unacceptable burden both for production and for sale.

A precondition, self-evident to every person skilled in the art, for the preparation of mixtures for carrying out the process according to the invention is the choice of those active substances or active substance forms or of those effervescent, dissolving and/or disintegrating systems which are at least briefly compatible with one another in aqueous solution. The fact that this compatibility need be present for only a short time is a further advantage of the present invention; it is therefore quite possible to choose compounds or systems which, on prolonged storage or on prolonged storage in solution (for example in ampoules) would react with one another in an undesirable manner and are therefore not suitable in this form for the patient to take. Many such compounds or systems are, however, sufficiently stable in aqueous solution for the few seconds or minutes which at the most elapse between the preparation of the solution or suspension by the process according to the invention and intake by the patient, because—particularly at room temperature—they undergo hydrolysis or react with one another in some other way only after a relatively long time.

The process according to the invention has proven useful particularly in the treatment of cardiac insufficiency and/or of hypertension, the individual adjustment of a patient to the daily required dose and distribution of this dose of the required medicaments over the period of time. In this treatment, it is in fact necessary to operate to a very particular degree with different medicaments and different doses, it being necessary occasionally to adjust, i.e. to change, the dose in the course of the treatment, sometimes even in relatively short time intervals. The process according to the invention therefore constitutes considerable advance particularly here.

Less critical although not without advantage is the use of the process according to the invention for the elimination of deficiency symptoms, where the dose is often unproblematic or at least uncritical and can therefore be left to the patient himself, for example as in the case of the so-called OTC preparations, as are usual, for example, for vitamin, calcium, magnesium or trace element doses.

The process according to the invention can also expediently be used in the treatment of asthma by combining, for example, antiallergics, e.g. ketotifen, with secretolytic agents or mucolytic agents, such as, for example, acetylcysteine, bromhexine or ambroxol, or with oral beta-mimetics, such as, for example, terbutalin or salbutamol.

Another application is in ulcer therapy by combination of H2-antagonists, for example cimetidine or ranitidine, with bismuth preparations and/or sucralfate. In this case, the combined treatment is particularly interesting because, for example, bismuth preparations are administered over a period of 2 to 4 weeks for the treatment of Campylobacter Pylori while the H2-blockers are administered over 6 to 8 weeks to reduce the acid secretion. The combination of H2-blockers with sucralfate in the acute phase would also be useful. When H2-blockers are discontinued, a considerable increase in acid secretion is often associated with recurrence. It is therefore often necessary to carry out prophylaxis with low doses (for example half tablets) to prevent recurrence.

Finally, the treatment or prevention of osteoporosis is also a preferred application of the process according to the invention, for example by combination of calcium preparations with fluorine preparations, for example the sodium fluorophosphate and/or diphosphonates. Particularly in the therapy with diphosphonates, for example etidronate, an intermittent treatment simultaneously with calcium preparations is carried out. Such treatment schemes are also combined with sodium fluorophosphate. In particular intermittent treatment with soluble or disintegrating tablets is expedient for such combinations. The combination of calcium preparations with estrogen or estrogen combination preparations is once again to be recommended for the prophylaxis of osteoporosis.

For all Examples mentioned, it is true that the preparation of a "cocktail" of different active substances in the form of soluble or disintegrating tablets means that the patient has to take only one preparation. The "cock-

EXAMPLE 1

A 60 year old patient has hypertension with symptoms of cardiac insufficiency. 20 mg of ACE inhibitor (e.g. enalapril), as a gradually increasing dose over a few days, and 20 mg of furosemide are administered daily as continuous therapy. If this is not sufficient within a few days, 1×20 mg or 2×10 mg of calcium antagonist (e.g. nifedipin) per day are administered. However, if the patient has varicose veins, the calcium antagonist should be replaced by increasing the dose of the ACE inhibitor.

EXAMPLE 2

A patient with hypertension and indications of cardiac insufficiency receives 20 mg of nifedipin daily. With the presence of varicose veins, edemas of the leg occurred. For this reason, he additionally receives furosemide, beginning with 20 mg/d; the dose may be increased to 30–40 mg/d in the course of the treatment, particularly if the symptoms of cardiac insufficiency increase (congested lungs, swelling of the legs).

EXAMPLE 3

A 45 year old patient weighing 85 kg has had chronic hypertension for 10 years. He is administered, for example, 10 mg of atenolol and 25 mg of hydrochlorothiazide daily; if the patient succeeds in losing 10 kg, the atenolol dose can be reduced to 50 mg daily. If the pulse is slowed down excessively during the therapy of the beta-blocker, the beta-blocker is replaced with a calcium antagonist. If the hypertension does not decrease within a few days, the beta-blocker dose must be increased correspondingly.

EXAMPLE 4

A patient with chronic asthmoid bronchitis initially receives 3×25 mg of salbutamol and 3×30 mg of ambroxol per day. The doses are reduced as recovery progresses.

EXAMPLE 5

A 55 year old woman with menopause-related symptoms and/or signs of incipient osteoporosis initially receives 50 mg of estradiol and 1000 mg of a suitable, calcium preparation per day; with sensible nutrition, the latter can soon be reduced to 500 mg daily.

EXAMPLE 6

A 61 year old patient has suffered from diabetes mellitus for 10 years and from hypertension for about 5 years.

Previously relatively well stabilized with metoprolol in sustained-release form (Beloc Duriles) as metoprolol tartrate 200 mg and glibenclamide (5 mg each morning). After the occurrence of severe, acute, obstructive bronchitis, it was necessary to change over to 10 mg of enalapril in the mornings and, owing to a deterioration in the diabetic metabolic state, to increase to 5 mg of glibenclamide in the morning and 5 mg at night. Also an additional dose of terbutalin 0.25 mg as a metered aerosol, 2 metered doses 3×daily, and acetylcysteine 2×100 mg. Thereafter, there was a substantial improvement in the obstruction and good stabilization of blood pressure and diabetes.

EXAMPLE 7

A 64 year old female patient suffering from hypertension had been well stabilized with 5 mg lisinopril for 7 years. Owing to an increasing sensation of nausea and diarrhea, an examination was carried out out and the laboratory values indicated substantially increased creatinine and hypercalemia. Immediate discontinuation of lisinopril and, in addition to strict monitoring and infusion therapy, changeover to nifedipin 2×10 mg and furosemide 40 mg in the morning. Then, after pronounced diuresis, substantial remission of the renal parameters and of the hypercalemia.

EXAMPLE 8

A 56 year old patient suffers from coronary heart disease (heart attack 5 years ago) and has been suffering from hypertension for 3 years. Since then well stabilized with nifedipin 2×20 mg and atenolol 50 mg in the morning. Sudden change in the blood pressure with systolic values over 200, additional administration of 25 mg of hydrochlorothiazide 3×weekly, but no ideal stabilization. Then changeover to captopril 3×12.5 mg and atenolol 50 mg+hydrochlorothiazide 3×25 mg per week. Then satisfactory RR values syst. between 140 and 160, drastic between 80 and 95 mmHg.

EXAMPLE 9

A 28 year old woman has been suffering from exogenic allergic bronchial asthma for 10 years. Has since been taking ketotifen 2×1 mg, sometimes 2×2 mg daily. After an acute infection of the upper respiratory tract, deterioration of the obstruction. Thereafter additional dose of erythromycin 3×500 mg and acetylcysteine 2×100 mg. After 3 days, development of an allergic exanthema, necessitating further changeover to doxycycline 100 mg 2×daily and administration of ambroxol 75 mg 2×daily. Remission of the exanthema and improvement of the obstruction and of the infection.

EXAMPLE 10

A 75 year old patient suffers from severe osteoporosis and has therefore been treated with fluorine-calcium preparation for years. Owing to gastric symptoms (no endoscopy or X-ray), additionally receives 2×2 g of sucralfate. After acute deterioration of the lumbago, administration of diclofenac 2×50 mg, whereupon the gastric symptoms increased. Gastroscopy revealed a duodenal ulcer. After discontinuation of diclofenac and an additional administration of cimetidine 800 mg at night in addition to the sucralfate, the gastric symptoms disappeared. The osteoporosis is additionally treated with etidronate 2×200 mg intermittently.

EXAMPLE 11

A 32 year old patient suffers from a recurring duodenal ulcer. Repeatedly treated in the past with cimetidine 800 mg at night and in addition sucralfate. Gastroscopy and biopsy gave a positive finding. Thereafter administration of bismuth nitrate oxide 3×350 mg over 4 weeks. Gastroscopy examination showed healed ulcer. Further check after one year indicated a normal situation.

EXAMPLE 12

A 53 year old gracile, blonde woman has been in the menopause since the age of 49.

During the gynaecological examination, she is advised to have a densitometry of the vertebrae, which reveals incipient osteoporosis. The doctor then recommends prophylaxis with an estrogen-gestagen preparation and calcium 500 mg daily.

EXAMPLE 13

A 35 year old patient has been taking metaprolol 2×50 mg and magnosolv for 1 month owing to cardiac arrhythmias (superventricular and ventricular extrasystoles) and has since suffered from disturbed sleep and depression. Omission of the night-time dose reduces the symptoms, but increased arrhythmias occur in the night. After changing the beta-blocker (from lipophilic metaprolol to hydrophilic atenolol), these symptoms disappeared.

EXAMPLE 14

A 47 year old with chronic obstructive bronchitis has been under treatment for years with clenbuterol 0.02 mg as required. Owing to a deterioration, the dose was increased to 3×0.02 mg daily. Additional infection (bacterial) and therefore therapy with cotrimoxazole 2×1 tablet and, owing to viscous mucous, bromhexine 8 mg 3 x daily with a large quantity of liquid. This is followed by a rapid improvement both of the expectoration and of the shortness of breath.

To adminster the various active substances mentioned in the above Examples, tablets of the following compositions are prepared according to the invention:

Acetylcysteine soluble tablet:
- 200 mg of acetylcysteine
- 320 mg of mannitol
- 342 mg of citric acid
- 160 mg of tartaric acid
- 287 mg of sodium bicarbonate
- 33 mg of polyvinylpyrrolidone
- 20 mg of flavor
- 10 mg of aspartame Estrogen/medroxyprogesterone disintegrating effervescent tablet:
- 2.0 mg of estradiol valerate
- 20.0 mg of medroxyprogesterone acetate
- 33.0 mg of polyvinylpyrrolidone
- 25.0 mg of polyvinylpyrrolidone XL
- 350.0 mg of citric acid
- 280.0 mg of sodium bicarbonate
- 0.2 mg of dioctylsulfosuccinate
- 167.0 mg of mannitol Calcium effervescent tablet:
- 2500 mg of calcium carbonate
- 4270 mg of citric acid
- 150 mg of gluconic acid deltalactone
- 8 mg of saccharin sodium
- 50 mg of flavor
- 27 mg of polyethylene glycol Estrogen calcium against osteoporosis with initiation of withdrawal bleeding:
- Calcium effervescent tablet+estrogen soluble tablet for 70 days
- Calcium+estrogen+medroxyprogesterone for 2 weeks Only calcium for 1 week Estrogen soluble tablet:
- 2 mg of estradiol valerate
- 7 mg of polyvinylpyrrolidone
- 33 mg of lactose
- 426 mg of citric acid
- 315 mg of sodium bicarbonate
- 25 mg of potassium carbonate Salbutamol soluble tablet:
- 2.8 mg of salbutamol sulfate
- 425.0 mg citric acid
- 10.0 mg of sodium citrate
- 286.0 mg of sodium bicarbonate
- 40.0 mg of sodium carbonate
- 67.0 mg of mannitol
- 4.0 mg of saccharin sodium
- 15.0 mg of flavor The standard oral dose is 2.8 mg of salbutamol sulfate, corresponding to 2 mg of salbutamol.

Enalapril soluble tablet:
- 20 mg of enalapril
- 142 mg of mannitol
- 710 mg of citric acid
- 86 mg of tartaric acid
- 290 mg of sodium bicarbonate
- 50 mg of sodium carbonate
- 4 mg of saccharin sodium
- 20 mg of flavor The tablet is provided with a score so that exactly 10 mg, 20 mg or twice the 20 mg dose (=2 tablets) are used for preparation of the cocktail.

Nifedipin disintegrating tablet:
- 10 mg of nifedipin
- 20 mg of maize starch
- 28 mg of polyvinylpyrrolidone (crosslinked)
- 70 mg of polyvinylpyrrolidone
- 350 mg of sodium bicarbonate
- 410 mg of citric acid
- 42 mg of Avicel Furosemide disintegrating effervescent tablet:
- 40.0 mg of furosemide
- 36.00 mg of maize starch
- 20.00 mg of polyvinylpyrrolidone (crosslinked)
- 720.00 mg of tartaric acid
- 375.00 mg of sodium bicarbonate
- 15.00 mg of aspartame
- 20.00 mg of flavor
- 0.15 mg of sodium dioctylsulfosuccinate A score permits the individual dose of 20 mg of furosemide.

Atenolol effervescent tablet:
- 200 mg of atenolol
- 510 mg of citric acid
- 40 mg of fumaric acid
- 2 mg of sodium citrate
- 100 mg of potassium bicarbonate
- 243 mg of sodium bicarbonate
- 45 mg of mannitol
- 62 mg of lactose
- 10 mg of aspartame
- 15 mg of flavor A score permits the individual dose. Angina pectoris: dose 50–400 mg/day Atenolol soluble tablet:
- 100 mg of atenolol
- 43 mg of malic acid
- 291 mg of citric acid
- 220 mg of sodium bicarbonate
- 37 mg of potassium bicarbonate
- 50 mg of magnesium carbonate
- 86 mg of mannitol
- 5 mg of aspartame
- 10 mg of flavor A score permits the individual dose.
Hypertension: Dose 50–200 mg/day Angina pectoris: Dose 50–400 mg/day.

Abroxol soluble tablet:
  33 mg of ambroxol hydrochloride
  470 mg of tartaric acid
  34 mg of potassium carbonate
  310 mg of sodium bicarbonate
  45 mg of glucose
  4 mg of saccharin sodium
  15 mg of flavor Sucralfate dispersion granules:
  2000 mg of sucralfate
  1130 mg of mannitol
  115 mg of Avicel
  86 mg of polyvinylpyrrolidone XL
  23 mg of polyvinylpyrrolidone
  30 mg of aspartame
  20 mg of flavor Bismuth nitrate soluble tablet:
  350 mg of bismuth nitrate
  1320 mg of tartaric acid
  54 mg of lactose
  131 mg of mannitol
  870 mg of sodium bicarbonate
  3 mg of saccharin sodium
  28 mg of sodium cyclamate
  30 mg of flavor Ranitidine soluble tablet:
  200 mg of ranitidine
  430 mg of citric acid
  38 mg of potassium bicarbonate
  290 mg of sodium bicarbonate
  37 mg of sodium carbonate
  15 mg of aspartame
  10 mg of flavor

We claim:

1. A process for the administration of an aqueous solution or dispersion of at least two different pharmaceutically active substances comprising
  (1) selecting and providing a separate, predetermined dosage amount for each of at least two different and distinct pharmaceutical preparations, each of the pharmaceutical preparations being portioned individually and each being in a separate form selected from the group consisting of soluble tablets, disintegrating tablets, soluble granules and disintegrating granules, each of which preparations contains a pharmaceutically active substance or an active substance combination different from that which each other preparation contains,
  (2) dissolving or suspending each of the separate, predetermined dosage amounts of each of the pharmaceutical preparations in one and the same quantity of water, the pharmaceutically active substances being at least briefly compatible with one another in aqueous solution;
  (3) orally administering said aqueous solution or dispersion, during the at least brief period of substance compatibility, to a patient in need thereof; and
  (4) repeating steps 1–3 at least once with at least one of the separate, predetermined dosage amounts differing from that selected and provided in step 1.

2. A process as claimed in claim 1 wherein at least one of the tablets is used only as a fragment.

3. A process as claimed in claim 1, wherein at least one of the preparations weighs less than 2000 mg.

4. A process as claimed in claim 1 wherein at least one of the preparations contains a diuretic and at least one of the further preparations contains a beta-blocker or a vasodilator.

5. A process as claimed in claim 4, wherein the diuretic is selected from the group consisting of hydrochlorothiazide and furosemide.

6. A process as claimed in claim 4, wherein the vasodilator is selected from the group consisting of naftidrofuryl, calcium antagonists, ACE inhibitors and alpha-1-blockers.

7. A process as claimed in claim 3 wherein at least one of the preparations weighs less than 1500 mg.

8. A process as claimed in claim 7 wherein at least one of the preparations weighs less than 1000 mg.

* * * * *